(12) United States Patent
Lynch et al.

(10) Patent No.: US 10,607,726 B2
(45) Date of Patent: Mar. 31, 2020

(54) SYSTEM FOR ANONYMIZING AND AGGREGATING PROTECTED HEALTH INFORMATION

(71) Applicant: Accenture Global Services Limited, Dublin (IE)

(72) Inventors: Cecil O. Lynch, Granite Bay, CA (US); Dennis Carroll, Leander, TX (US); Andrew J. Truscott, Spring, TX (US)

(73) Assignee: ACCENTURE GLOBAL SERVICES LIMITED, Dublin (IE)

( * ) Notice: Subject to any disclaimer, the term of this patent is extended or adjusted under 35 U.S.C. 154(b) by 522 days.

(21) Appl. No.: 14/092,168

(22) Filed: Nov. 27, 2013

(65) Prior Publication Data
US 2015/0149208 A1    May 28, 2015

(51) Int. Cl.
*G16H 10/60*   (2018.01)
*G06F 21/62*   (2013.01)
*G06F 19/00*   (2018.01)

(52) U.S. Cl.
CPC ............. *G16H 10/60* (2018.01); *G06F 19/00* (2013.01); *G06F 21/6254* (2013.01)

(58) Field of Classification Search
CPC ...... G06Q 50/22; G06Q 50/24; G06F 19/345; G06F 19/322; G06F 19/3443
See application file for complete search history.

(56) References Cited

U.S. PATENT DOCUMENTS 6,397,224 B1   5/2002   Zubeldia et al.
7,668,820 B2   2/2010   Zuleba
7,865,376 B2   1/2011   Ober et al.
8,275,850 B2   9/2012   Kohan et al.
9,202,078 B2   12/2015  Abuelsaad
(Continued)

FOREIGN PATENT DOCUMENTS

WO    9855977 A1    12/1998
WO    2012166633 A1    12/2012

OTHER PUBLICATIONS

Second Examination report for Australian Application No. 2014265125, dated May 21, 2015.
(Continued)

*Primary Examiner* — Jonathan Durant
(74) *Attorney, Agent, or Firm* — Brinks Gilson & Lione

(57) ABSTRACT

A patient anonymizing system includes a plurality of hashing appliances and data sources. Each appliance receives medical records containing at least confidential protected health information (PHI). A salt value is appended to each confidential PHI, and a hash is generated, which replaces the confidential PHI to generate an anonymized record. A master patient index server aggregates the anonymized records. A vector and cluster matching engine determines if the anonymized record matches a unique patient identifier corresponding to a second anonymized record. A comparison vector is generated by comparing hash values of the confidential PHI with hash values in the second anonymized record, and is crossed with a confidence vector having weights based on match conditions. This produces a match confidence level, which is compared to a threshold. If the threshold is met, the anonymized record is mapped to the unique patient identifier associated with the second record.

20 Claims, 10 Drawing Sheets

(56) References Cited

U.S. PATENT DOCUMENTS

| | | | |
|---|---|---|---|
| 2002/0073099 A1* | 6/2002 | Gilbert | G06F 17/3061 |
| 2002/0073138 A1 | 6/2002 | Gilbert et al. | |
| 2003/0187713 A1* | 10/2003 | Hood | G06Q 30/0204 |
| | | | 705/7.33 |
| 2004/0025057 A1* | 2/2004 | Cook | G06Q 10/107 |
| | | | 726/28 |
| 2004/0107205 A1* | 6/2004 | Burdick | G06F 17/30303 |
| 2005/0165623 A1* | 7/2005 | Landi | G06Q 50/22 |
| | | | 705/2 |
| 2005/0236474 A1* | 10/2005 | Onuma | G06F 19/322 |
| | | | 235/382 |
| 2005/0256741 A1 | 11/2005 | Kohan et al. | |
| 2006/0020611 A1 | 1/2006 | Gilbert et al. | |
| 2006/0147083 A1* | 7/2006 | Piersol | G06F 21/16 |
| | | | 382/100 |
| 2007/0192139 A1* | 8/2007 | Cookson | G06F 19/322 |
| | | | 705/3 |
| 2008/0240425 A1* | 10/2008 | Rosales | G06F 21/6254 |
| | | | 380/28 |
| 2009/0150289 A1 | 11/2009 | Joe | |
| 2011/0010563 A1 | 1/2011 | Lee et al. | |
| 2011/0112862 A1* | 5/2011 | Yu | G06F 17/30867 |
| | | | 705/3 |
| 2012/0159637 A1* | 6/2012 | Dove | G06F 21/6254 |
| | | | 726/26 |
| 2012/0303616 A1* | 11/2012 | Abuelsaad | G06F 21/6227 |
| | | | 707/736 |

OTHER PUBLICATIONS

Examination report for Australian Application No. 2014265125, dated Dec. 23, 2014.
Extended European Search Report for EP 14194259.9, Completed Jun. 30, 2015.
First Examination report for Australian Application No. 2015275323, dated Oct. 27, 2016.
First Examination report for Australian Application No. 2016202995, dated Aug. 1, 2017.
Office Action issued on corresponding Indian application No. 5680/CHE/2014 dated Feb. 26, 2019, 5 pages.

* cited by examiner

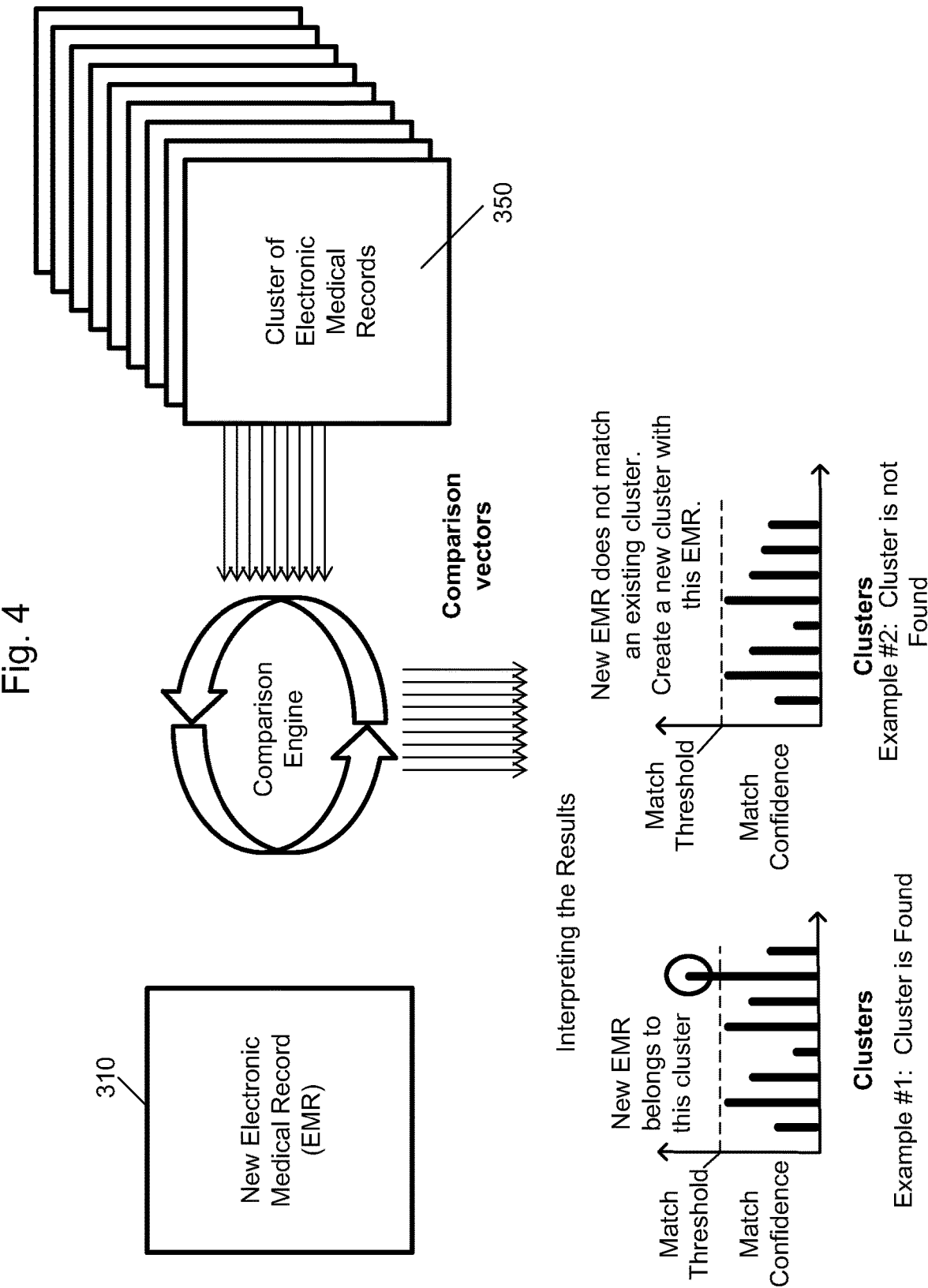

SYSTEM FOR ANONYMIZING AND AGGREGATING PROTECTED HEALTH INFORMATION

BACKGROUND OF THE INVENTION

1. Technical Field

This disclosure relates to aggregating patient medical records, and in particular, to aggregating and organizing medical records in a manner that protects the identity of the patient.

2. Background

Patient medical records are increasingly becoming digitized and stored in computer databases. Data privacy and security issues are thus paramount, as well as compliance with applicable laws and regulations. For example, in the United States, the HIPAA (Health Insurance Portability And Accountability Act) requires that patient medical records be kept confidential, and not released to third parties without authorization. Yet, it is advantageous for different entities to have access certain medical records for purposes of research, clinical studies, and diagnosis. However, many regulations, including HIPAA, do not permit unrelated or independent entities to aggregate medical records as such aggregation could permit the entity to identify persons associated with the medical records, resulting in a privacy breach.

Further, even when medical records are properly obtained, such records may be incomplete, erroneous, and/or ambiguous. Thus, aggregating and associating medical records corresponding to a particular patient is difficult, irrespective of the privacy and compliance issues.

Accordingly, a need exists to allow analysis of patient medical records in a protected (i.e., anonymous) fashion by aggregating and identifying medical records as belonging to a common patient without revealing the identity of the patient. This is useful in research, clinical studies, or when identifying medical conditions, particularly when such patient medical records are obtained from unrelated databases or source systems.

SUMMARY

Described herein is a system for anonymizing and aggregating protected health information (PHI) from a plurality of data sources includes a plurality of data hashing appliances each operatively coupled to the respective data source, each hashing appliance configured to receive from the respective data source, one or more patient medical records, where each patient medical record contains at least one data element of confidential protected health information (PHI), and a master record number (MRN) assigned by the respective data source. Each hashing appliance is configured to append a salt value to each data element of confidential PHI in the patient medical record, generate a hash value for each salted data element of confidential PHI, and replace the data element of confidential PHI with the generated hash value to generate an anonymized patient medical record.

Also included is a master patient index server coupled to a data repository, which is configured to aggregate a plurality of anonymized patient medical records received from the plurality of data hashing appliances. A vector and cluster matching engine operatively coupled to the master patient index server and the data repository is configured to determine if the anonymized patient medical record received from respective hashing appliances matches a unique patient identifier corresponding to at least a second anonymized patient medical record stored in the data repository. The matching is determined by generating a comparison vector by comparing the hash values corresponding to the data elements of confidential PHI in the received anonymized patient medical record with the corresponding hash values in the second anonymized patient medical record, generating a confidence vector by assigning weights based on predetermined match conditions, crossing the comparison vector with the confidence vector to obtain a match confidence level, comparing the match confidence level to a predetermined threshold to determine if the received anonymized patient medical record corresponds to the unique patient identifier, and mapping the received anonymized patient medical record to the unique patient identifier if the confidence level is greater than the predetermined threshold.

Using the system for anonymizing and aggregating protected health information, research can be done retrospectively across a broad population with more complete information on each patient while still maintaining confidentiality of the person and complying with HIPAA regulations.

Other embodiments of the systems, methods, features, and their corresponding advantages will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The described system for anonymizing and aggregating protected health information (PHI) may be better understood with reference to the following drawings and the description. The components in the figures are not necessarily to scale, emphasis instead being placed upon illustrating the principles of the invention. Moreover, in the figures, like reference numerals designate corresponding parts throughout the different views.

FIG. 4 is a pictorial diagram illustrating clustering of new electronic medical records based on the comparison vector and confidence vectors of FIG. 3.

DETAILED DESCRIPTION OF THE PREFERRED EMBODIMENTS

Figure 1:
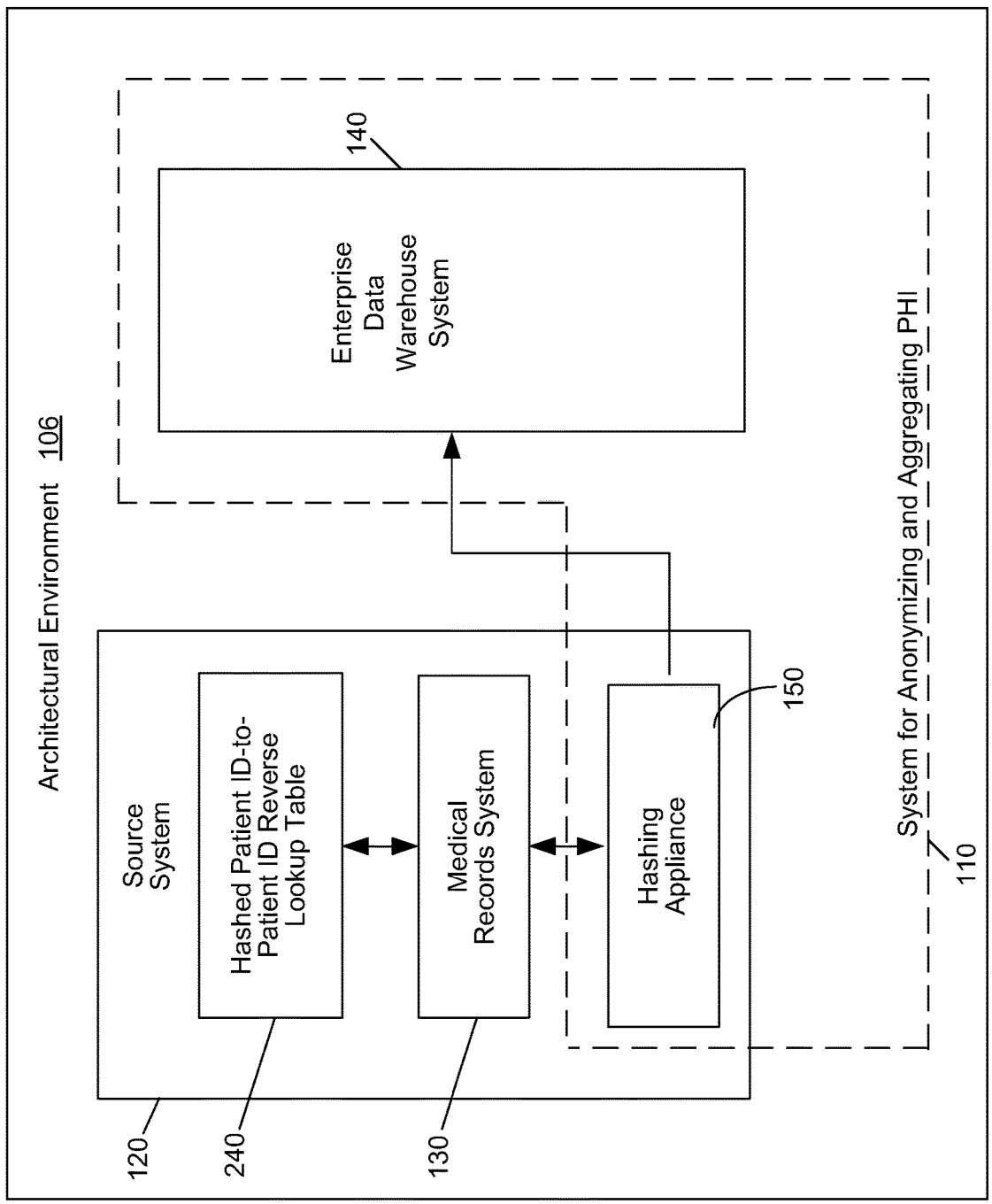
FIG. 1 is a block diagram of an environment in which a system for anonymizing and aggregating protected health information may operate, according to a specific embodiment.

FIG. 1 is a high-level hardware block diagram of an architectural environment in which a system for anonymizing and aggregating protected health information 110 may operate. The architectural environment 100 may include a plurality of source systems 120, each of which may include a plurality of medical records systems 130. The architectural environment 100 may also include an enterprise data warehouse system 140 operatively coupled to one or more source systems 120. The system for anonymizing and aggregating protected health information (PHI) 110 may functionally include the enterprise data warehouse system 140, and may also include an anonymizer hashing appliance 150 embedded in the source system 120. However, the placement of each component within the overall architectural environment 100 may vary to include additional components or fewer components, depending on the specific embodiment. Note that the phrase "protected health information" may be used interchangeably with the phrase "patient health information," and may be broader in scope than may be used or explicitly defined per HIPAA.

Figure 2:
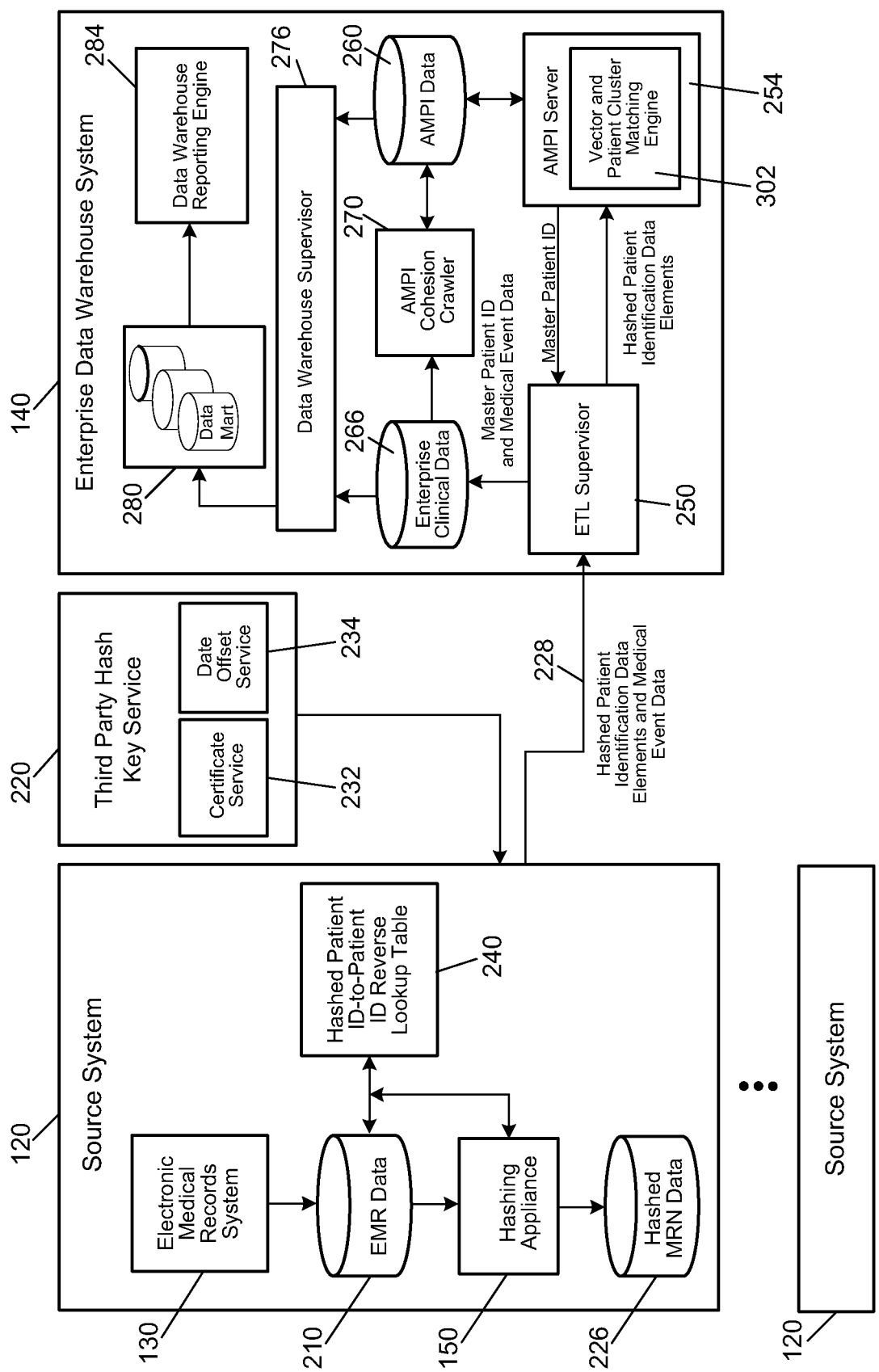
FIG. 2 is a block diagram of the environment of FIG. 1 in greater detail, according to a specific embodiment.

FIG. 2 shows the architectural environment 110 in greater detail. The architectural environment 110 in some embodiments may include a plurality of the source systems 120, which are frequently disparate and unrelated source systems. Such multiple source systems 120 may be associated with various providers, such as hospitals, medical offices, pharmacies, pathology providers, and the like. For a particular patient, it is often the case that the various providers do not share protected health information with other such providers, thus the protected health information or records may be maintained on separate, unrelated, and disparate computer systems.

As shown in FIG. 2, each source system 120 preferably includes the embedded hashing appliance 150. The source system 120 may include the electronic medical records system 130 coupled to an electronic medical records database 210 or data storage, either which may also be a remotely located component. The hashing appliance or component 150 receives input from the electronic medical records database 210 and receives hashing salt values and date offset values from a third party hash key service 220. The hashing appliance 150 provides output to a hashed master record number database 226. As is understood in the art, a hash is the fixed-length resulting output of a cryptographic algorithm (such as SHA-1) that has been applied to an input data value. The practical effect of this function is to anonymize the input data value.

The hashing appliance 150 may provide output in the form of hashed data elements 228 to the enterprise data warehouse system 140 as part of an electronic medical record (EMR). The third party hash key service 220 further includes a certificate service 232 and a data offset service 234. The source system 120 may also include a hashed system patient ID-to-patient ID reverse lookup table 240, which may be used to identify an actual patient based upon a request from the enterprise data warehouse system 140. The hashed system patient ID-to-patient ID reverse lookup table 240 may include the identity of the actual patient (unencrypted patient identifier) and a corresponding hashed value of the MRN, which was inserted into the record that was previously sent to the enterprise data warehouse system 140, as will be discussed below. The hashed system patient ID-to-patient ID reverse lookup table 240 may reside in or be operatively coupled to the EMR database 210, or may be included in or operatively coupled to the hashed MRN database 226.

The enterprise data warehouse system 140 may include an ETL (extract, transform, and load) supervisor 250, which receives hashed patient identification data elements from the anonymizing hashing appliance 150. The ETL supervisor 250 may be operatively coupled to an AMPI server (anonymized master patient index) 254. The AMPI server 254 is configured to store the encrypted and anonymized patient records in an AMPI data component 260 or memory storage, and its main function is to generate a single identifier that essentially aggregates all qualifying anonymized patient records so as to identify or map all such records to a single anonymous patient. Note that none of the data received from the hashing appliance 150 contain any confidential protected health information in readable or discernible form. All such data has been converted to a hash value, the contents of which cannot be decoded to arrive at the original value.

The ETL supervisor 250 may be operatively coupled to an enterprise clinical database 266, which in turn may receive input from an AMPI cohesion crawler 270, and may provide output to a data warehouse supervisor 276. The AMPI data storage 260 may be operatively coupled to the AMPI server 254, the AMPI cohesion crawler 270, and the data warehouse supervisor 276. In turn, the data warehouse supervisor 276 may be operatively coupled to a data mart 280, which may provide output to a data warehouse reporting engine 284.

Note that for any particular source system 120, all records of a particular patient will be assigned a unique master record number (MRN) by that source system. Thus, a particular source system 120 may supply to the hashing appliance 150, many records of a particular patient, which would all have the same MRN. Each record preferably includes a source identifier that identifies the source system that produced the record. Such a common MRN (at least from one source system 120) permits the records to be easily grouped together to reflect association with a single person.

However, when multiple source systems are involved, for example a first source system and a second source system, because the source systems may be separate and independent, the second source system may assign a totally new MRN to the same patient whose records also exist in the first source system, as neither source system is privy to the information contained in the other source system. Alternatively, the second source system may happen to assign the same MRN to a different person, thus two different persons may happen to have the same MRN because the first source system is completely separate and independent from the second source system. Also note that although the AMPI data may group all records associated with a single individual, those records may have a plurality of different MRNs because such MRNs were assigned by separate and independent source systems 120. Thus, an additional list or linked list may exist for each patient, which lists the various MRNs that may be associated with that patient. Essentially, the MRN for a particular patient may be considered to be an "alias" and such an alias may not be unique to that patient. The handling of ambiguity of in MRNs is discussed below with reference to FIG. 3.

With respect to FIG. 2, the enterprise clinical database 266 stores the anonymized electronic patient records received directly from each hashing appliance, while the AMPI data storage 260 stores the anonymized electronic patient records, and such records are associated with the specific source system that the MRN that the particular source system 120 may have assigned.

But as mentioned above, there may be some ambiguity associated with the MRN, thus, after all records have been processed by the AMPI cohesion crawler 270 and the vector and patent cluster matching engine 302, each record is associated with a unique AMPI unifying number associated with a particular patient. Note that because each patient record includes the source identifier as well as the MRN, all records having the same MRN generated by one particular identified source system 120 correspond to the same patient. Conversely, two patient records having different MRNs generated by the same source systems 120 correspond to two different patients. However, two patient records having the same MRN generated by different source system 120 are ambiguous and are not definitive by themselves in identifying the patient. It may be also that the source identifier does not identify a particular source system 120, where multiple source systems 120 are aggregated and operated by the same healthcare provider or organization, and the same source identifier could be used to represent healthcare providers so long as MRNs were uniquely assigned within the universe of source systems 120 operated by that healthcare provider or organization.

The combination of the AMPI data component 260 and the enterprise clinical data component 266 may provide all of the relevant data. The data warehouse supervisor acts as an interface so that an entity that may employ or access the system 110 can obtain the appropriate records. The data mart 280 may represent the specific data of interest, which may be a reduced subset of the electronic medical records, and may omit data that is not of interest to the entity that may employ or access the system 110.

Note that only data elements corresponding to confidential protected health information of each patient health record are generally anonymized by the hashing appliance 150. If a data element is not confidential in nature nor could be used in any way to identify or help ascertain the identity of the patient, such data elements in the medical record may not be anonymized. Data elements containing confidential protected health information may include name, street address, zip code, date of birth, social security number, and the like. Dates of service are commonly recognized to be sensitive in nature (e.g., under HIPAA), but must be anonymized in a fashion that still permits mathematical comparisons to be conducted, as such information is necessary to permit useful analysis of the aggregated data. Conversely, data that need not be anonymized at all may include diagnosis information, test results, and the like.

As a general overview of the operation of the hashing appliance 150, a common salt value is used to create the hash corresponding to the each data element in the medical record containing confidential protected health information. If the same salt value and the same hash algorithm are used on the same data, such as a confidential patent data item, even if the data is culled from a different record or different source system, the ultimate hash value will be identical. In this way, data records corresponding to the same confidential protected health information can be aggregated because they should have a common hash value. Accordingly, each and every data element in the medical record corresponding to confidential protected health information is salted and hashed so as to render the confidential protected health information anonymous. The common salt value is obtained in a secure fashion (e.g., by exchange over a secure communications channel) from the third party hash key service 220 so as to introduce a data element unknown to the enterprise data warehouse system 140 into the hashes. In this manner, the enterprise data warehouse system 140 (or entity employing the enterprise data warehouse system 140) cannot decode or "reverse engineer" the hashed data elements even if the enterprise data warehouse system 140 knows which hashing algorithm was used to create the hashes.

Given a sufficient number of records, correspondence or "agreement" among a plurality of different anonymized data elements permits a confidence level to be achieved that indicates that the disparate medical data records indeed correspond to the same patient, even though the identity of the patient, and/or the confidential patent information, is unknown. Moreover, such confidential protected health information will be anonymous because the hash value cannot be decoded or "reverse engineered" to provide the confidential protected health information. Accordingly, after a patient record has been anonymized, a particular patient record having openly available patient data can be provided to an entity, such as an aggregation entity, namely an enterprise data warehouse system 140 (or entity employing an enterprise data warehouse system 140) for use in research, diagnosis and the like, because each data element corresponding to confidential protected health information in the record has been anonymized and is represented only by the hash value.

The hashing appliance 150 may be a hardware or software component that resides within the firewall or other security measures of the data source system 120 or owner of the patient data records. The hashing appliance 150 appears as a black-box component that receives data records from the source system 120 and hashes each and every confidential protected health information field in the record, and manages an offset for the date of service field so as to disguise the true date of service for that record. The date of service field in the record is preferably calculable and usable by the data aggregator or enterprise data warehouse system 140, and thus is preferably not fully anonymized because such dates are needed when performing analysis on the anonymized patient medical record. Thus, such dates of service are "disguised" with an offset value rather than being fully anonymized, thereby enabling evaluation of the timeliness of events relative to each other without disclosing the absolute date of the event.

The hashing appliance 150 also applies the common salt value received from the third party hash key service 220 to create the hashed data for the confidential data elements. As alluded to above, because the hash was produced using a salt value, running a "brute force" decoding process, for example, using a name dictionary to decode every name to obtain the hash key, would not crack the hash code because the hash value is not a "direct hash" of the confidential data. Rather, the hash value is the result of a hash of confidential data plus a random value, for example, a random integer or string. After the hashing appliance 150 has anonymized each confidential field of data in the medical record, the record, including the anonymized data and the non-anonymized data, are encrypted and transmitted to the ETL supervisor 150 of the enterprise data warehouse system 140.

As discussed above, the hashing appliance 150 performs a hash on each confidential data field of each patient record. Further, each confidential data field is hashed twice. Preferably, a first hash is a 256-bit hash function, such as an SHA-256 (Secure Hash Algorithm) hash algorithm. The first hash is then hashed a second time to create the final hash value, and the first hash value is destroyed along with the confidential data field. The second hash value then replaces the confidential data in the record. Preferably, the second hash algorithm may be a 128-bit (or shorter) hash function, and preferably is a different type of hash algorithm compared to the first hash algorithm, such as an SHA-128 hash algorithm. Any suitable hash function may be used. Note that because the second hash is a shorter hash than the first hash based on bit width, the second hash has lost data compared to the first hash. Because the first hash is destroyed and second hash is clearly missing information contained in the first hash, the hash cannot be decoded or reversed to obtain the original input to the first hash. The advantage of the smaller second hash is also that it takes less memory to store, increasing efficiency of the system 110.

Because the final hash value is a reduction hash, meaning a hash of a hash, and the first hash is destroyed along with the source confidential data, is it not possible for an attacker to associate the second hash value back to the original confidential data field. With respect to HIPAA, this process fully satisfies the applicable safe harbor rules for de-identification because the eventual hash is not derived from the confidential data field, rather, it is derived from an irreversible hash.

The hashing appliance 150 ultimately transmits the second and final hash value of the confidential data field as part of the data payload (which includes, non-confidential data of the patient record) to the enterprise data warehouse system 140. Note that because the confidential protected health information has been hashed and salted, and hashed a second time, anonymization of the confidential protected health information is irreversible. This means that neither the original owner of the data record residing on the source system 120 nor any component of the enterprise data warehouse 140 would be able to identify any of the confidential protected health information give the resulting anonymized data record, subject to one intentional process referred to as "re-identification" described below with respect to the source system 120.

The third party hash key service 220 is preferably separate and independent from either the source system 120 or any components of the enterprise data warehouse system 140 so as to maintain a secure environment and prevent intentional or unintentional collaboration. Because no other components of the architectural environment 100 have access to the third party hash key service 220, there no possibility that the hash key can be decoded and reveal the confidential protected health information during the hashing process. The third party hash key services 220 provides the common salt value and certificate service for data encryption to permit the hashing appliance 150 to create the hashed data elements.

In one embodiment, the third party hash key services 220 derives the salt value from a radio frequency seed value to generate a truly random integer value. Alternatively, a string value may be derived from the radio frequency seed source. However, the common salt value is not necessarily limited to an integer value, an integer value of any particular length, or a string. The common salt value may also be a randomized string, a rational number, or any suitable value derived from any random source. Any suitable technique for generating the common salt value may be used, such as, for example, a UNIX-based OWASP function, and the like. Note that the same "salt" value should be used on corresponding encrypted fields in each data source.

Note that some known systems may include a trusted third party to handle the various data records and deal with security measures. However, the third party hash key services 220 of embodiments of the system 110 is not a "trusted" third party service. The third party hash key services 220 is an independent component that supplies the common salt value and encryption support to two "untrusted" parties, namely the source system 120 and the enterprise data warehouse system 140, where neither component "trusts" the other component.

As mentioned above, the date offset service component 234 of the third party hash key service 220 provides an offset or "disguise" for the date of service field of each patient record. The offset value is not saved back into the patient record, but rather, the hashing appliance 150 saves the offset value, which may correspond the each master record number in the source system 120 in which the hashing appliance 150 is embedded. Certain dates, and in particular, dates of service associated with the medical record of the patient are prohibited in a fully de-identified patient record that meets the HIPAA safe harbor requirements. To accommodate these requirements, it is necessary to offset the dates in such a way so that the date offset is unknown to the data receiver. In order to have consistency across all data aggregators users of the system 100 that may receive usable data records from the enterprise data warehouse system 140, it is necessary to have consistency of the offset dates across all the data source systems 120. This allows calculations that are meaningful in data analysis without the use of actual dates. The following date offset method described below is consistent with those requirements.

In this process, the date is converted to an offset from a given base date, and the same base date is used for all data source systems 120. Thus, each date is merely an offset, for example, the value of −7, which corresponds to a date seven days prior to a base date. All dates, meaning the offset values, are relative to each other, which permits analysis of the data, such as population assessment and the like. In a first step to provide such date shifting, the date offset service 234 may generate a random number between 0 and −365. This implies that the range of dates would be limited to a one year time span, however, other values may be used so as to increase or decrease this time span. In other embodiments, a code for one of four seasons or quarters may be included to provide additional granularity. This integer value is then encrypted with a public key that the source system 120 provides to the hashing appliance 150. The hashing appliance 150 may receive the encrypted integer and associate this encrypted integer with the master record number (MRN) associated with this patient. Typically, this encrypted integer is defined and saved at the time the hashing appliance is installed in the source system 120.

Figure 3A:
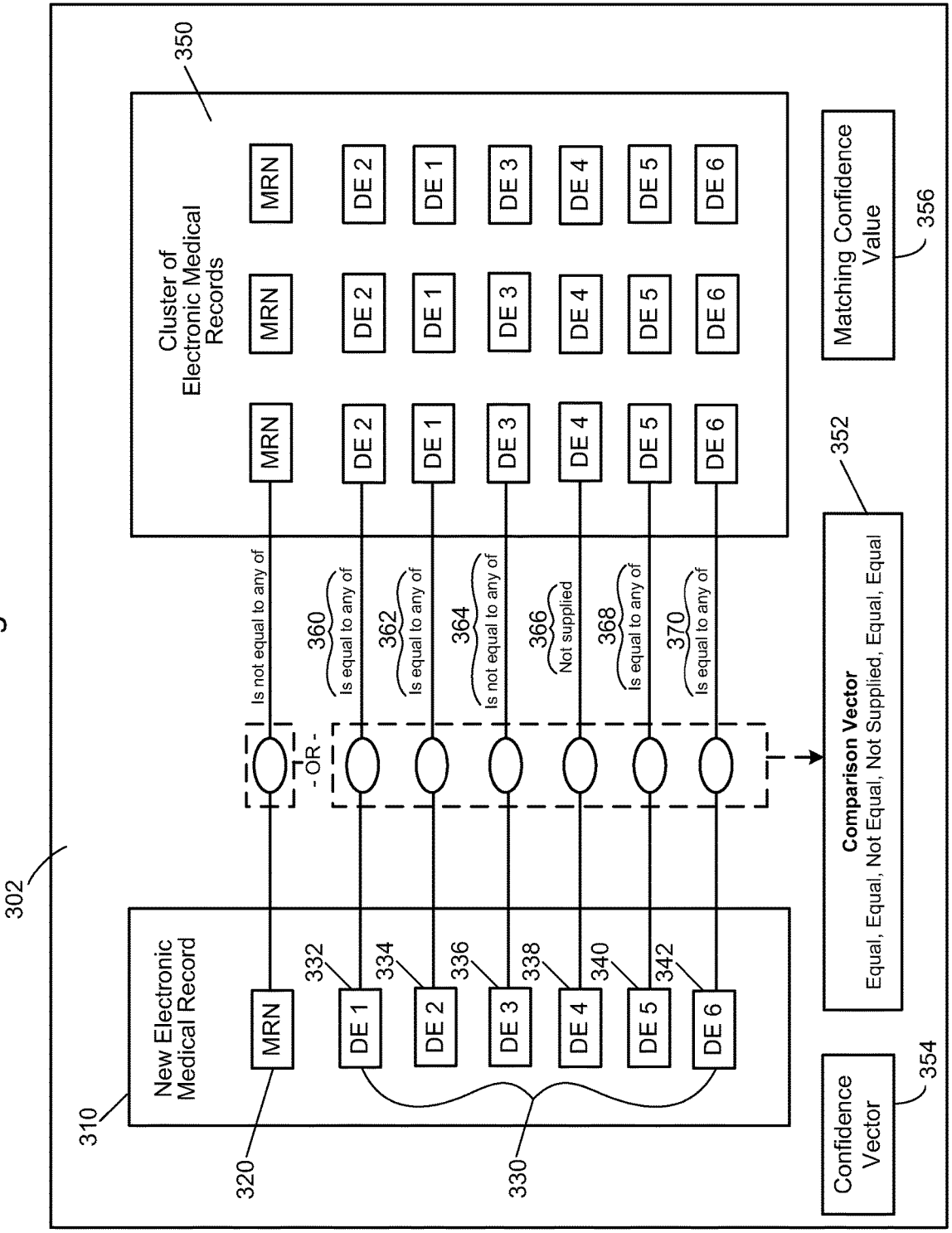
FIG. 3A is a pictorial diagram showing a mechanism for generating a comparison vector and confidence vector, according to a specific embodiment.
Figure 3B:
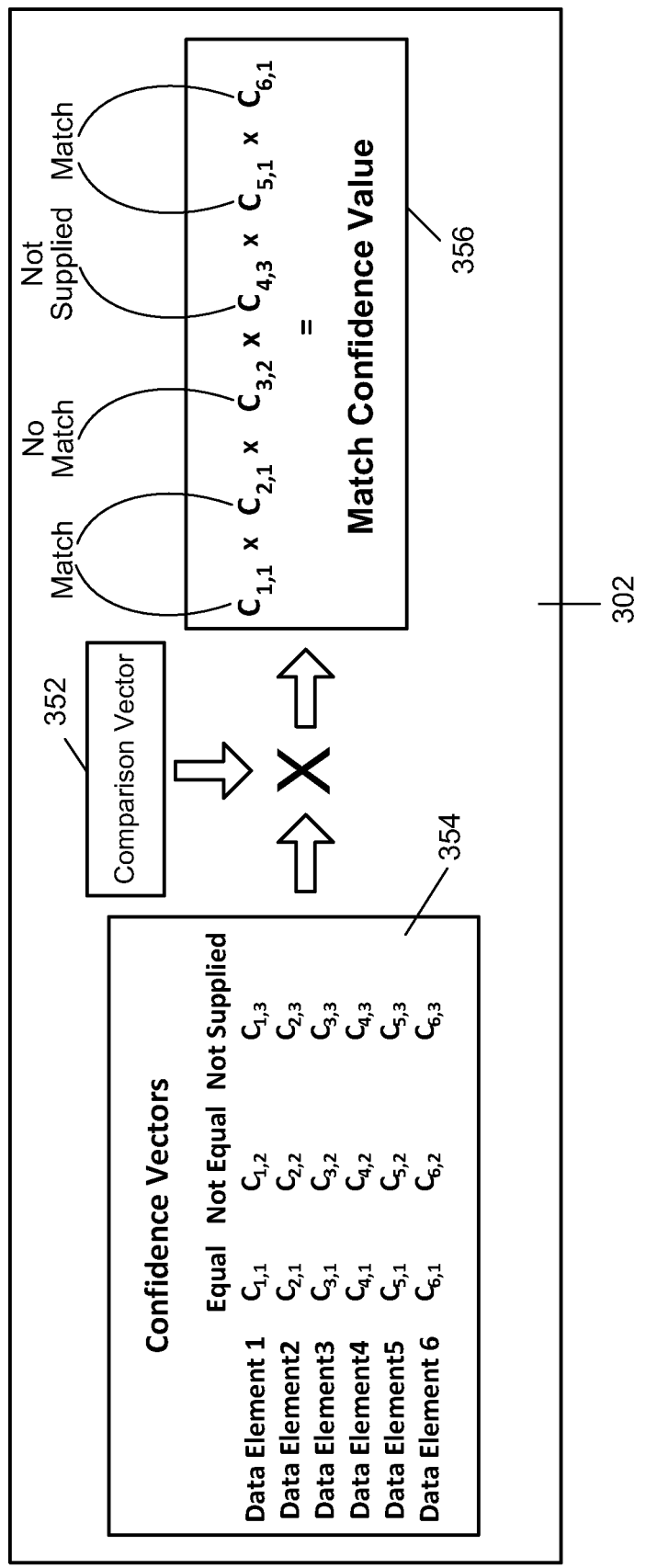
FIG. 3B is a continuation of FIG. 3A showing additional detail.

FIGS. 3A and 3B are pictorial representations showing a mechanism for generating a matching confidence value based on a confidence vector and a comparison vector. The matching confidence value essentially permits mapping all medical fields of one patient into a cluster of electronic medical records, all associated with that particular patient.

As described above with respect to the source system and corresponding MRN's, each electronic medical record includes a source identifier and record identifier or MRN, where the MRN is unique for all records coming from that source system 120. A mapping established between the source identifier and the MRN to a master record identifier, all subsequent instances of that MRN from that source system are mapped to the master record identifier and the contents of the elements are added to the valid values for each element in the master record vector. In one embodiment, the master recorder identifier and associated data are stored in the AMPI data component 260.

Further as discussed above, the enterprise data warehouse 140 receives the anonymized patient records from the hashing appliance 150. Once received and stored by the AMPI server 254, the anonymized records should somehow be associated or mapped together to build the record base associated with a particular patient, although the patient identity is unknown. The final result of such associating or mapping is a single unique identifier that is able to tie together or aggregate all of the records common to one particular patient. This is based on the premise that identical confidential data elements that have been reduced to a hash value will necessarily have identical hash values, although irreversible and un-decodable.

For example, if one patient record having a hash value in the name field was derived and anonymized from a record having the name field of "Cecil Lynch," a second record obtained from the same or from a different source having that same hash value may be a good candidate to associate with the first record, where both records would be mapped to the same patient ("Cecil Lynch"). However, this in not necessarily the case, as there may be more than one patient having the name of Cecil Lynch. To determine if two such records are truly a match to the same patient, a vector and patient cluster matching engine 302 of FIGS. 3A and 3B is employed to provide a confidence level or matching confidence value, which if sufficiently high, indicates that the records belong to the same patient. The patient cluster matching engine 302 may be part of the part of the AMPI server or may be a separate and independent component thereof.

The vector and patient cluster matching engine 302 attempts to map to a common patient, all records that have a very high probability of corresponding to that patient. However, some data may be ambiguous, incomplete, or inaccurate. For example, a name in one record may be misspelled, or an abbreviation of the name may be used, and the like. Accordingly, identical hash values for name field may not be the same even though they actually correspond to the same patient. The converse may also be true. However, given a sufficient number of records for a particular patient, the AMPI cohesion crawler 270 in conjunction with the patient cluster matching engine 302 may able to build a form of dictionary or variance dictionary to list and keep track of acceptable post-encrypted (post-hashed) data element values (variations) for each anonymized confidential data field.

Also, in some cases, the MRN may provide a high-confidence field to determine if one patient record should be grouped with a cluster of records for a particular patient. For example, if an MRN of a received patient record matches another MRN in a cluster, and both MRNs were generated by the same source system 120 (or group of source systems 120), as indicated by the source identifier number, there is a high likelihood that the patients are the same.

FIGS. 3A and 3B show a newly received anonymized electronic medical record (EMR) 310, as indicated by its master record number (MRN) 320 The anonymized medical record 310 may contain a plurality of data elements 330, for example, shown as DE1 (332), DE2 (334), DE3 (336), DE4 (338), DE5 (340), and DE6 (342) in one embodiment. If the hashed master record number 320 matches, the record 310 is said to belong to a target cluster 350, meaning that it corresponds to a single patient having a plurality or target cluster of records. However, because the MRNs for a particular patient and for different patients may have been generated by separate and independent source systems 120, the MRN may not match even though the records actually correspond to the same patient, and further, such MRN may indeed match, even though they correspond to different patients. But if the MRNs do match and both MRNs were generated by the same source system 120, as indicated by the source system identification number in the record, then there is a very high matching confidence.

If the master record number 320 does not match, the record may still correspond to the above-mentioned patient (target cluster), but not with 100% certainty. In this case, each hashed values of the data elements are compared to corresponding accumulated values of each electronic medical record cluster to search for correspondence. The results are used to build a comparison vector 352 that when crossed with a confidence vector 354, provides a match confidence value 356.

In the example of FIGS. 3A and 3B, for the given data element DE, the matching process shows the following example conditions:

a) hashed data element DE1 (332) "is equal to any of" (360) data elements in the target cluster 350;
b) hashed data element DE2 (334) "is equal to any of" (362) data elements in the target cluster 350;
c) hashed data element DE3 (336) "is not equal to any of" (364) data elements in the target cluster 350;
d) hashed data element DE4 (338) "is not supplied" and is omitted from the matching (366) data elements in the target cluster 350;
e) hashed data element DE5 (340) "is equal to any of" (368) data elements in the target cluster 350;
f) hashed data element DE6 (342) "is equal to any of" (370) data elements in the target cluster 350;

The comparison vector 352 is then calculated based on the matching 35 criteria, which is crossed with the confidence vector 354 to provide the match confidence value 356. The comparison vector 352 may be a one-dimensional array or vector that holds the matching conditions for each data element 330. There may be one of three conditions for each data element 330, namely "not equal," "equal," and "not supplied." For convenience, each condition may be given a particular value, such as 0, 1, and 2, respectively. Thus, the comparison vector of FIG. 3A for the new MRN received may appear as: [1, 1, 0, 2, 1, 1] in vector format.

The confidence vector 354 may be a vector or array having a number of rows equal to the number of data elements, and a number of columns equal to the number of possible conditions of each data element, namely three. For example, if 6 data elements exist in the EMR 310, the confidence vector may be represented by a 6×3 array.

When the comparison vector is crossed with the confidence vector, the match confidence level 356 is produced. As shown in FIG. 3B, the match confidence level 356 is the product of six components, each component corresponding to one of the six data elements in this specific example. The first two components represent a match condition, the third component represents a not matched condition, the fourth component represents a not supplied condition, and the last two components represent a match condition.

In one embodiment, a confidence value for each missing indicator may be applied based on from historical statistics. For example, missing gender may correspond to a different confidence value than a missing date-of-birth. Moreover, missing gender may correspond to a different confidence value than an non-matching gender. Further, a weight corresponding to a not supplied condition may be calculated according to the particular field in the patient medical record that is missing. For example, a missing gender field may be assigned a different weight (confidence value) than missing date-of-birth field. Moreover, a missing gender field may be assigned a different weight (confidence value) than an non-matching gender field. Additionally, the calculated weight values may be tunable or may vary based on statistical information, historical information, or predetermined rules.

As an example, the AMPI server 254 may receive two different patient records, meaning they have different master record numbers 320, but may in fact, correspond to the same patient. The various data elements are compared in accordance with FIG. 3, and for example, the hashed address fields may match, but the hashed name fields may indicate a mismatch. However, the matching hashed address field may add to the level of confidence that these two records indeed belong to the same patient.

Assuming that the match confidence value calculated 356 is greater than a predetermined value, the two records are then mapped as belonging to the same patient, and the new record is mapped into the target cluster 350. In this case, although the hashed name fields do not match, the system does not know what such a mismatch means. For example, the hash value mismatch of the name field may have been due to a slightly different name in the name field, such as "Bob" and "Rob" in the original confidential name data field of the respective records. Of course, such a slight difference in names would hash to a completely different value, thus resulting in the mismatch. Note that, for example, a "first name" field from an incoming electronic medical record is compared to each "first name" accumulated for that MRN. Thus, an incoming electronic medical record can match on a first name for the MRN that came from one particular data source system 120 and can also match on a last name for the MRN that came from an entirely different data source system. Such matching and "slight difference" recognition may be applied to all hashed fields of the MRN.

However, because the two records are mapped to the same patient due to the high match confidence level based on the product of all of the hashed fields, the hashed name fields for both records may set as "related" or "equivalent" in the matching or variance dictionary. Thus, subsequent records received by the AMPI server 254 will not necessarily be mismatched merely because of the above-mentioned difference in the hashed name field. In other words, either name will now be accepted for the new record 310 received to be mapped into the target cluster of records 350, assuming other data in the new record 310 results in a sufficiently high match confidence value 356 with the target cluster 350, as described immediately above.

Figure 5:
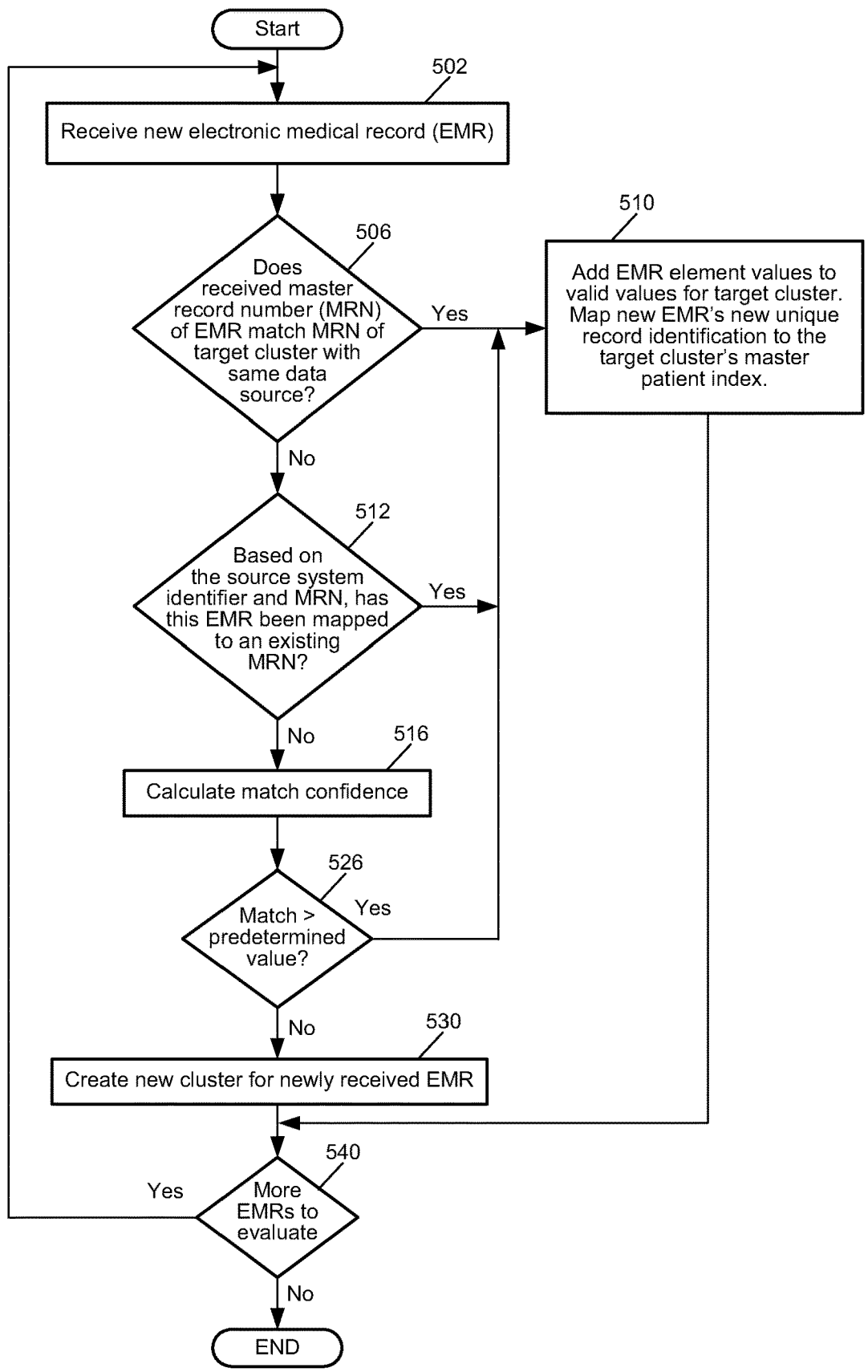
FIG. 5 is a flowchart depicting acceptance or rejection of a new record with respect to a target cluster.

FIG. 4 shows the above described process in pictorial format, while FIG. 5 is a flowchart depicting acceptance or rejection of a new record with respect to a target cluster. First, a new electronic medical record (EMR 310) is received (step 502). Next, the master record number (MRN 320) of the target cluster 350 is compared to the MRN of the newly received EMR 310 (step 506). If a match exists, the newly received EMR 310 is set as a match for the target cluster 350, meaning that all such records correspond to the same patient, and the electronic medical record's element values are added to valid values for target cluster 350, and the new EMR's unique record identifier is mapped to the target cluster's master patient index (step 510).

If the MRN of the newly received EMR does not match the MRN 320 of the target cluster 350, the source identifier and the MRN are checked to determine if this electronic medical record has already been mapped to an existing MRN (step 512). If so, the electronic medical record's element values are added to the valid values for the target cluster (step 510).

If this electronic medical record has not been mapped to an existing MRN, a match confidence is calculated (step 516). If the match confidence value exceeds the predetermined value or threshold (step 526), a match is declared and the newly received EMR 310 is mapped with the target cluster (step 510). If the match confidence value is not sufficiently high, a new cluster is created (step 530) for the newly received EMR 310. If additional new EMRs exist (step 540), the above process is repeated (step 502) for the newly received EMR 310.

Figure 6:
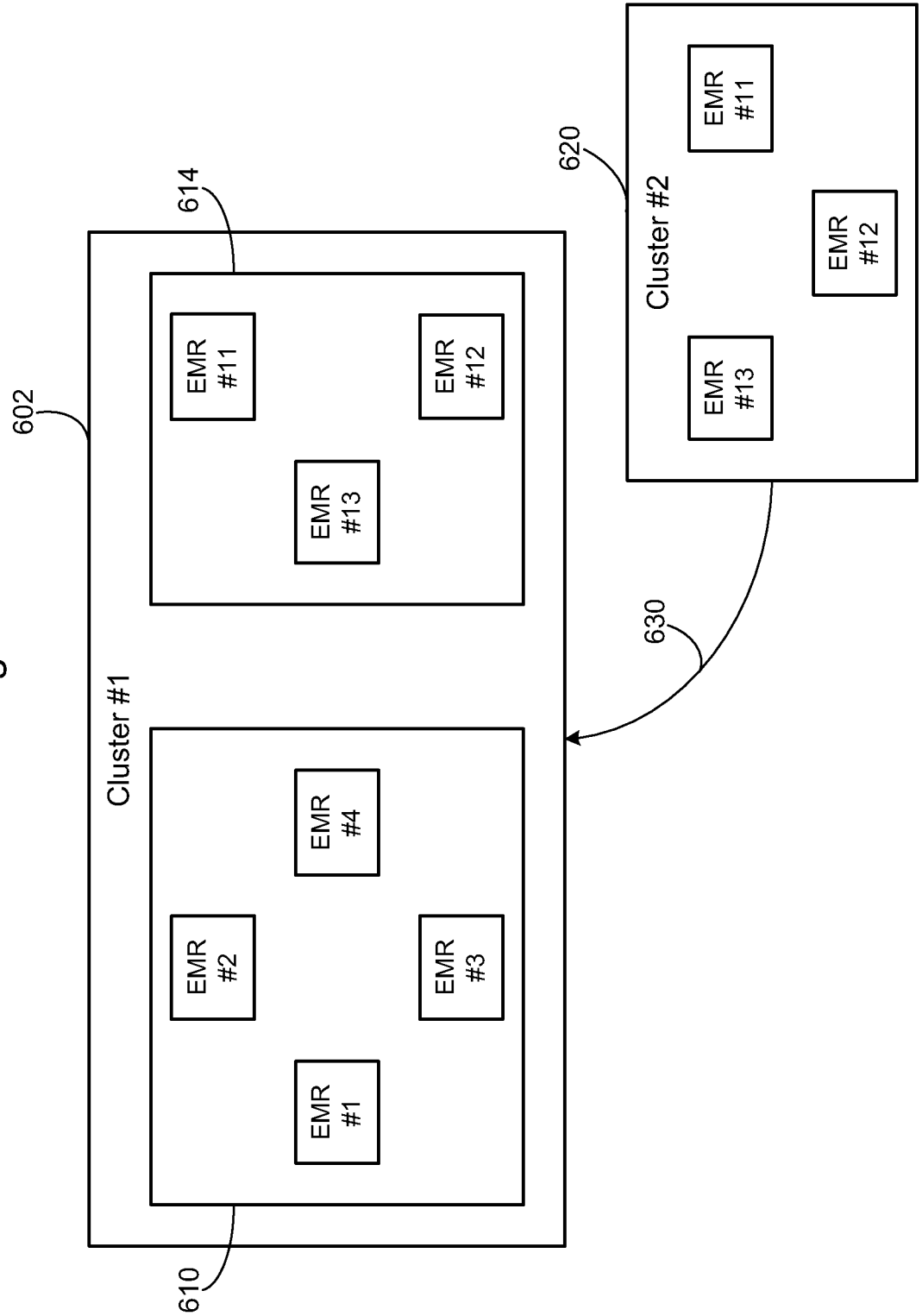
FIG. 6 is a diagram depicting a cohesion crawler process configured to join a new record to a target cluster.

Referring now to FIG. 6, an example of the process performed by the AMPI cohesion crawler 270 of FIG. 2 is shown, where two clusters are joined into a single cluster. The AMPI cohesion crawler 270 performs a continuous background process to inspect the data records as they are received so as to machine learn and link or map the various data records to common patients. As shown in this specific example, a cluster #1 602 includes electronic medical records nos. 1-4 (610) and electronic medical records 11-13 (614). Assume that the group of four EMRs (610) corresponds to a patient named George Smith. In this example, EMR #4 is a record from Nationwide Radiology and includes a hash of George's SSN while the other records do not.

Next, assume George Smith moves to a new city and is cared for by a new primary care physician. The new physician does not include George's SSN in his patient record. Worse still, the new physician switches George's first and middle names. Record EMR #13 is added that does not strongly connected to any existing cluster, so a new cluster is created 620 consisting only of the new EMR #13. In this example, another record (EMR #11) is added by a pharmacist for George that is most strongly connected to the record in the new cluster 620. However, it also does not include the hash of the SSN.

Assume that a record is now added by Nationwide Radiology using George's new address but also using his SSN. The cohesion crawler determines that the two records (EMR #11 and EMR #12) actually belong together because of the hash of the common SSN in each, thus joining all of George's records together notwithstanding instances of George's two addresses causing two subgroups. The records for EMR #11, EMR #12, and EMR #13 are now joined to the first cluster 602, as shown by line 630. Future records with either of George's address will be added to this cluster 602.

Figure 7:
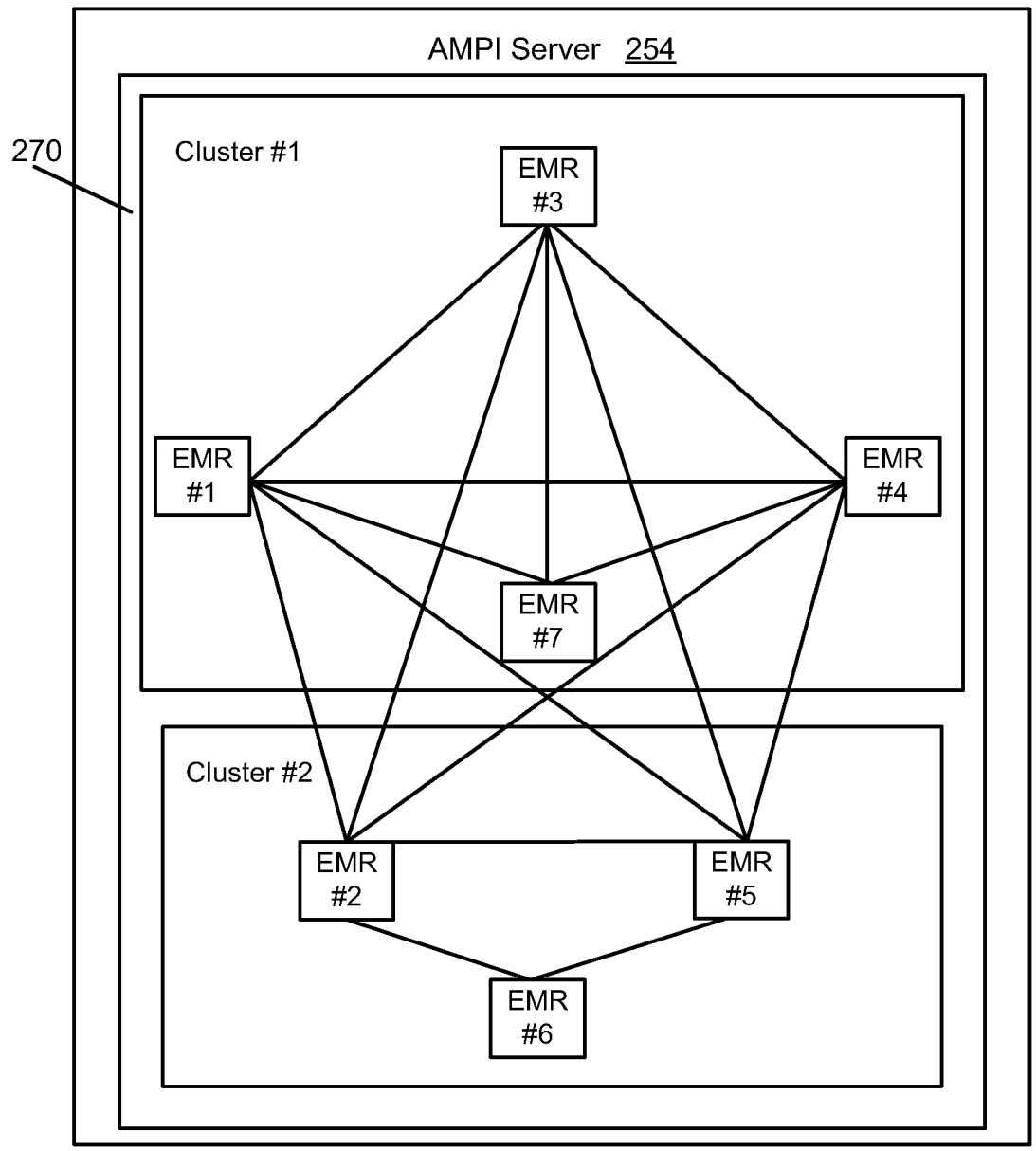
FIG. 7 is a diagram depicting a cohesion crawler process configured to split a single cluster into two clusters.

FIG. 7 is an example that depicts an "inverse" process performed by the AMPI cohesion crawler 270 to remedy a situation where EMRs were erroneously added to a target cluster, and shows a single cluster split into two separate clusters. In this example, twins named George Michael Foreman and George Thomas Foreman live at the same address and except for their middle name hashes, all hashes of identifying information possessed by the AMPI are the same. The twins are taken to an emergency room following an automobile accident. Social security numbers are collected for each twin. The hashes of the different SSN's combined with the hashes of the different middle names weaken the cohesion of the group such that it is recognizable that there are in fact two distinct groups with a single master patient identifier. Thus, there is an erroneous joining of EMR's in the cluster. The AMPI cohesion crawler 270 examines the group, recognizes that two distinct groups exist, and segregates them creating a new group for one of the twins.

Figure 8:
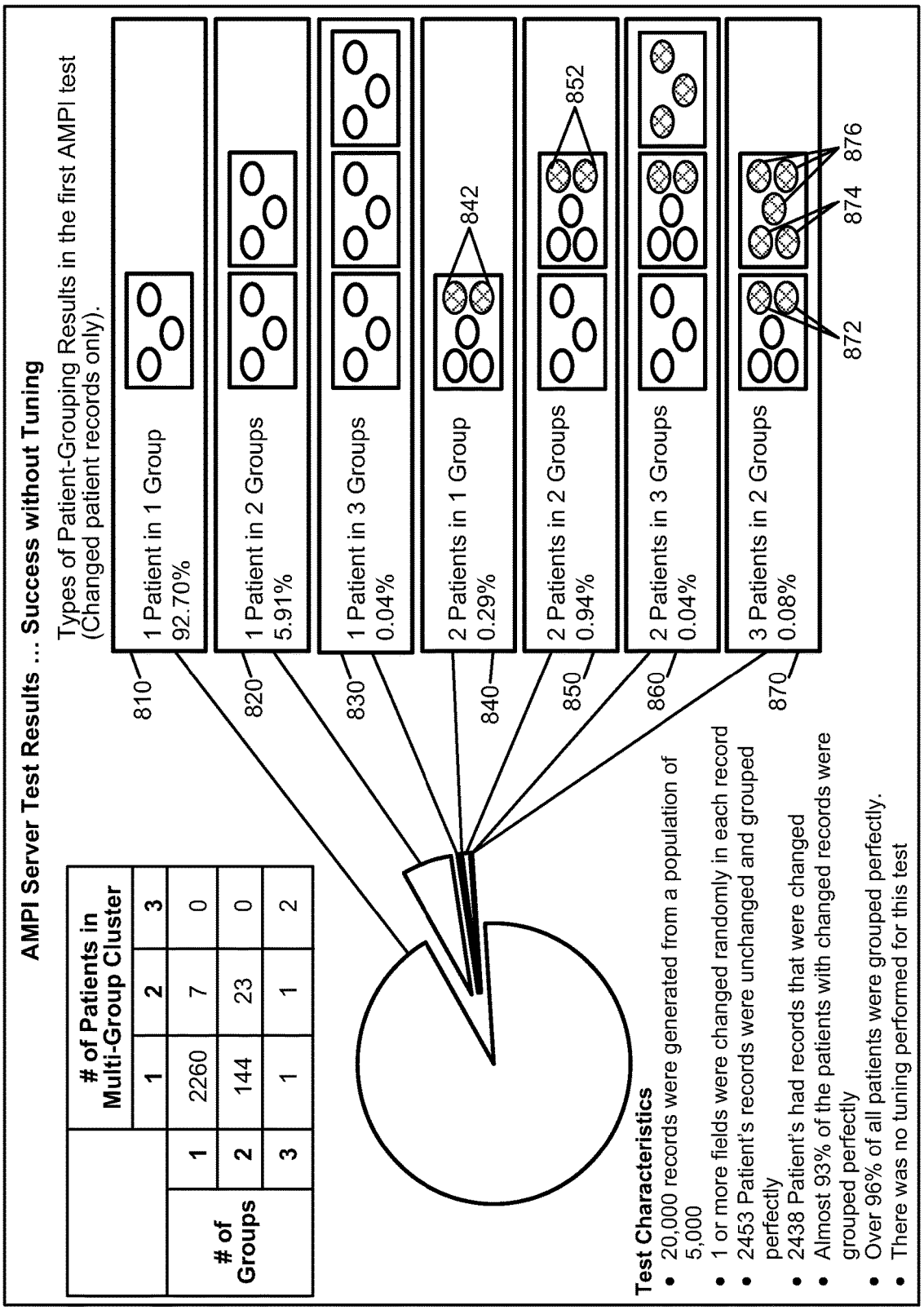
FIG. 8 shows empirical results of processing a plurality of patient records.

FIG. 8 is a diagram showing empirical test results for 20,000 test records processed by the system for anonymizing and aggregating patient records 110. The records are based on actual records with a representative sampling of common names, gender splits, age, demographics, and the like consistent with distributions and geographic definitions found in the United States. Further, certain of the records were edited to introduce typical errors or ambiguities in the data elements to test the efficacy of the system 110. A first frame 810 shows about a 93% success rate where every record for a person is correctly linked to exactly one MRN. A second frame 820 shows about a 6% rate where one patient is inadvertently split into two groups with two MRNs but no other patient is added to either MRN. A third frame 830 shows an extremely low rate of 0.04% where one patient is inadvertently split into three groups. A fourth frame 840 shows about a 0.29% rate where a second patient 842 is inadvertently included in a first patient group. A fifth frame 850 shows about a 0.94% rate where two patients 852 are shown in two groups. A sixth frame 860 shows about a 0.04% rate where two patients are shown in three groups. And a seventh frame 870 shows about a 0.08% rate where three patients (872, 874, 876) are shown in two groups.

Although the focus of the system of anonymizing and aggregating PHI 100 is to anonymize protected health information so that a patient cannot be identified from the aggregated data, there are certain situations when the patient should be identified or notified of certain medical conditions for their own health and safety. For example, an entity performing research based on the records provided by the system 100, may discover that certain bio-markers inspected may indicate that those persons may contract cancer. Thus, it is important that such individuals be contacted to inform them of the discovered risk. Because each patient record includes the MRN and the identifier of the source system that assigned that MRN, the source system 120 would be able to identify the actual patient associated with that MRN using the hashed system patient ID-to-patient ID reverse lookup table 240.

In one embodiment, when the hashing appliance 150 hashes the data field corresponding to the MRN, the data source 120 retains a table, such as the hashed system patient ID-to-patient ID reverse lookup table 240, which may associate the hashed MRN value with the true identity of the patient. This is referred to as re-identification. Preferably, the hashing appliance 150 performs only a single hash on the record indicator used for re-identification, rather than a double hash. When the patent should be notified due to a discovered health risk, the enterprise data warehouse system 140 may send back to the source system the encrypted and singly hashed MRN value of the record of the patient of interest.

Because the record or cluster of records of the patient to be contacted has a corresponding MRN that the source system 120 originally assigned, the source system 120 can decrypt the received MRN and look up the decrypted hash value in the hashed system patient ID-to-patient ID reverse lookup table 240, and ascertain the identity of the patient for purposes of notification. The system 100 and the source system 120 may encrypt the various hashed fields using known public key encryption methods.

Figure 9:
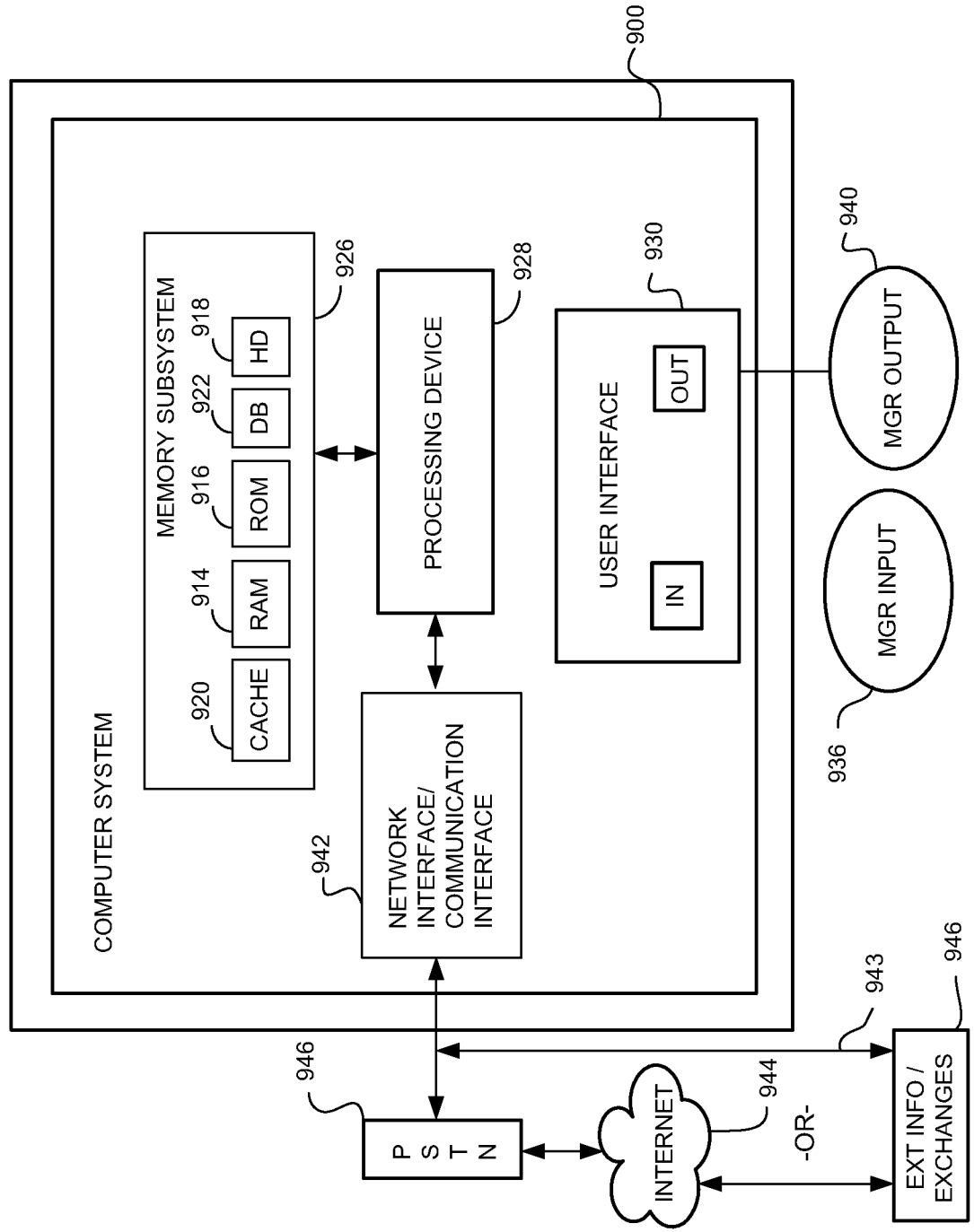
FIG. 9 is a representative computer system that may embody the system for anonymizing and aggregating protected health information, according to one embodiment.

FIG. 9 is a high-level hardware block diagram of a computer system 900, which may be part of the system for anonymizing and aggregating protected health information 110, or the system for anonymizing and aggregating protected health information 110 may be embodied as the computer system 900 cooperating with computer hardware components and/or as computer-implemented methods. The hashing appliance 150 may also be embodied in the computer system 900 as shown, with some variation. The system for anonymizing and aggregating protected health information 110 may include a plurality of software modules or subsystems operatively coupled to or residing in the computer system 900. The modules or subsystems, such as the hashing appliance 150, the third party hash key service 220, the AMPI server 254, the AMPI cohesion crawler 270, and other components of the enterprise data warehouse system 140 may be implemented in hardware, software, firmware, or any combination of hardware, software, and firmware, and may or may not reside within a single physical or logical space. For example, the modules or subsystems referred to in this document and which may or may not be shown in the drawings, may be remotely located from each other and may be coupled by a communication network.

The computer system 900 may be a personal computer, server, or other suitable computer, and may include various hardware components, such as RAM 914, ROM 916, hard disk storage 918, cache memory 920, database storage 922, and the like (also referred to as "memory subsystem 926"). The computer system 900 may include any suitable processing device 928, such as a computer, microprocessor, RISC processor (reduced instruction set computer), CISC processor (complex instruction set computer), mainframe computer, work station, single-chip computer, distributed processor, server, controller, micro-controller, discrete logic computer, and the like, as is known in the art. For example, the processing device 928 may be an Intel Pentium® microprocessor, x86 compatible microprocessor, or equivalent device, and may be incorporated into a server, a personal computer, or any suitable computing platform.

The memory subsystem 926 may include any suitable storage components, such as RAM, EPROM (electrically programmable ROM), flash memory, dynamic memory, static memory, FIFO (first-in, first-out) memory, LIFO (last-in, first-out) memory, circular memory, semiconductor memory, bubble memory, buffer memory, disk memory, optical memory, cache memory, and the like. Any suitable form of memory may be used, whether fixed storage on a magnetic medium, storage in a semiconductor device, or remote storage accessible through a communication link. A user or system manager interface 930 may be coupled to the computer system 900 and may include various input devices 936, such as switches selectable by the system manager and/or a keyboard. The user interface also may include suitable output devices 940, such as an LCD display, a CRT, various LED indicators, a printer, and/or a speech output device, as is known in the art.

To facilitate communication between the computer system 900 and external sources, a communication interface 942 may be operatively coupled to the computer system. The communication interface 942 may be, for example, a local area network, such as an Ethernet network, intranet, Internet, or other suitable network 944. The communication interface 942 may also be connected to a public switched telephone network (PSTN) 946 or POTS (plain old telephone system), which may facilitate communication via the Internet 944. Any suitable commercially available communication device or network may be used.

The logic, circuitry, and processing described above may be encoded or stored in a machine-readable or computer-readable medium such as a compact disc read only memory (CDROM), magnetic or optical disk, flash memory, random access memory (RAM) or read only memory (ROM), erasable programmable read only memory (EPROM) or other machine-readable medium as, for examples, instructions for execution by a processor, controller, or other processing device.

The medium may be implemented as any device that contains, stores, communicates, propagates, or transports executable instructions for use by or in connection with an instruction executable system, apparatus, or device. Alternatively or additionally, the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure calls; or as a combination of hardware and software.

In other implementations, the logic may be represented in a signal or a propagated-signal medium. For example, the instructions that implement the logic of any given program may take the form of an electronic, magnetic, optical, electromagnetic, infrared, or other type of signal. The systems described above may receive such a signal at a communication interface, such as an optical fiber interface, antenna, or other analog or digital signal interface, recover the instructions from the signal, store them in a machine-readable memory, and/or execute them with a processor.

The systems may include additional or different logic and may be implemented in many different ways. A processor may be implemented as a controller, microprocessor, microcontroller, application specific integrated circuit (ASIC), discrete logic, or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instructions may be parts of a single program, separate programs, or distributed across several memories and processors.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A system for anonymizing and aggregating protected health information (PHI) from a plurality of data sources, the system comprising:
a plurality of data hashing appliances each operatively coupled to a respective data source, each hashing appliance configured to receive from the respective data source, one or more patient medical records, each patient medical record containing at least one data element corresponding to confidential protected health information (PHI), and a master record number (MRN) assigned by the respective data source, each data hashing appliance configured to:
append a salt value to each data element corresponding to confidential PHI in each patient medical record;
generate a hash value for each data element corresponding to salted confidential PHI;
replace each data element corresponding to confidential PHI with the corresponding generated hash value to generate an anonymized patient medical record;
a master patient index server coupled to a data repository, configured to cluster a plurality of anonymized patient medical records received from the plurality of data hashing appliances under a unique patient identifier;
a vector and cluster matching engine operatively coupled to the master patient index server and the data repository that includes a processor and non-transitory computer readable media coupled to the processor for causing the processer to determine if a newly received anonymized patient medical record received from a hashing appliance is related to anonymized patient medical records clustered under the unique patient identifier by:
generating a comparison vector by comparing the hash values corresponding to the confidential PHI in the newly received anonymized patient medical record with corresponding hash values of the anonymized patient medical records clustered under the unique patient identifier;
providing a confidence vector that defines a two-dimensional matrix of elements, wherein:
each row in the two-dimensional matrix is associated with one field of possible fields of an anonymized patient medical record,
a first column of the two-dimensional matrix lists elements to be selected when a value of a field of the newly received anonymized patient medical record matches a value of a corresponding field in a cluster of anonymized patient medical records,
a second column of the two-dimensional matrix lists elements to be selected when the value of a field of the newly received anonymized patient medical record does not match any values of a corresponding field in a cluster of anonymized patient medical records, and
a third column of the two-dimensional matrix lists elements to be selected when the value of a field of the newly received anonymized patient medical record is not provided;
selecting elements of the confidence vector based on the comparison vector;
multiplying the selected elements together to thereby obtain a match confidence level, wherein the match confidence increases with an increase in a magnitude of the match confidence level;
comparing the match confidence level to a predetermined threshold; and
clustering the newly received anonymized patient medical record to the unique patient identifier if the confidence level is greater than the predetermined threshold.

2. The system according to claim 1, wherein a hash key service provides the salt value to the plurality of hashing appliances, the hash key service being external from the data source, the master patient index server, and the data repository.

3. The system according to claim 1, wherein each patient medical record includes data elements corresponding to confidential PHI and non-confidential PHI, wherein only data elements corresponding to confidential PHI are anonymized at the respective data source prior to transmission to the master patient index server.

4. The system according to claim 1, wherein a plurality of predetermined match conditions include a data match condition, a data not matched condition, and a data not supplied condition.

5. The system according to claim 1, wherein:
each data element corresponding to confidential PHI is processed using a first hash algorithm to generate a first hash value;
each first hash value is processed using a second hash algorithm to generate a second hash value;
each first hash value is destroyed; and
each data element corresponding to confidential PHI in the patent medical record is replaced by the corresponding second hash value, such that the corresponding second hash value cannot be decoded so as to identify the value of the original data element corresponding to confidential PHI.

6. The system according to claim 5, wherein the corresponding second hash values will be identical if the value of the original data element corresponding to confidential PHI were identical.

7. The system according to claim 5, wherein the second hash algorithm has hash bit-width smaller than a hash bit-width of the first hash algorithm so that a data is lost from a first hash in the creation of a corresponding second hash, wherein the second hash value cannot be decoded or reversed to decode the value of the original data element corresponding to confidential PHI.

8. The system according to claim 1, wherein the elements defined in the confidence vector are based on a not equal condition, an equal condition, and a not supplied condition with respect to hash values corresponding to the confidential PHI between the received anonymized patient medical record and the second anonymized patient medical record.

9. The system according to claim 8,
wherein for each field, the confidence vector defines an element for each not supplied condition;
wherein an element associated with a not supplied condition of a first field in the patient medical record is different from an element associated with a not supplied condition of a second field in the patient medical record.

10. The system according to claim 1 wherein the key hash service provides an offset value to replace each date of service field in each patient medical record using an integer valued saved in the data repository so as to offset the dates of service.

11. The system according to claim 1, wherein each hashing appliance is operatively coupled within the respective data source, and the respective data source is separate remotely located from the master patient index server and the data repository.

12. The system according to claim 1, wherein each hashing appliance generates a hash value for the MRN of the patient medical record, and encrypts the hashed MRN using a key provided by the respective data source, and wherein the data source saves the hashed MRN in a MRN-to-patient table to provide a correspondence between the hashed MRN value and an identity of the patient associated with each patient medical record.

13. The system according to claim 12, wherein:
based on a re-identification request corresponding to a targeted MRN, the master patient index server transmits the encrypted targeted MRN to the source system that originally assigned the MRN to the patient record; and
the source system decrypts the targeted MRN and locates the targeted MRN in the table to re-identify the patient associated with the targeted MRN.

14. A method for anonymizing and aggregating protected health information (PHI) from a plurality of data sources, the method comprising:
transmitting, by one data source of the plurality, a plurality of patient medical records, to a hashing appliance operatively coupled to the one data source, each patient medical record containing at least one data element corresponding to confidential protected health information (PHI), the hashing appliance:
appending a salt value to each data element corresponding to confidential PHI in each patient medical record;
generating a hash value for each data element corresponding to salted confidential PHI;
replacing each data element corresponding to confidential PHI with the corresponding generated hash value to generate an anonymized patient medical record;
transmitting a plurality of anonymized patient medical records, to a data repository;
clustering, by the data repository, the plurality of anonymized patient medical records under a unique patient identifier;
determining, using a vector and cluster matching engine operatively coupled to the data repository, if the a newly received anonymized patient medical record from the hashing appliance is related to anonymized patient medical records clustered under the unique patient identifier by:
generating a comparison vector by comparing the hash values corresponding to the confidential PHI in the newly received anonymized patient medical record with the hash values of the anonymized patient medical records clustered under the unique patient identifier;
providing a confidence vector that defines a two-dimensional matrix of elements, wherein:
each row in the two-dimensional matrix is associated with one field of possible fields of an anonymized patient medical record,
a first column of the two-dimensional matrix lists elements to be selected when a value of a field of the newly received anonymized patient medical record matches a value of a corresponding field in a cluster of anonymized patient medical records,
a second column of the two-dimensional matrix lists elements to be selected when the value of a field of the newly received anonymized patient medical record does not match any values of a corresponding field in a cluster of anonymized patient medical records, and
a third column of the two-dimensional matrix lists confidence values to be selected when the value of a field of the newly received anonymized patient medical record is not provided;
selecting elements of the confidence vector based on the comparison vector;
multiplying the selected elements together to thereby obtain a match confidence level, wherein the match confidence increases with an increase in a magnitude of the match confidence level;
comparing the match confidence level to a predetermined threshold; and
clustering the newly received anonymized patient medical record to the unique patient identifier if the confidence level is greater than the predetermined threshold.

15. The method according to claim 14, wherein a subsystem, coupled via communication network to the source system, provides the salt value to the hashing appliance, and the subsystem is remotely located from the source system, the master patient index server, and the data repository.

16. The method according to claim 14, wherein:
each data element corresponding to confidential PHI is processed using a first hash algorithm to generate a first hash value;
each first hash value is processed using a second hash algorithm to generate a second hash value;
each first hash value is destroyed; and
data element corresponding to confidential PHI in each patent medical record is replaced by the corresponding second hash value, such that the corresponding second hash value cannot be decoded so as to identify the value of the original data element corresponding to confidential PHI.

17. The method according to claim 16, wherein the second hash algorithm has a hash bit-width smaller than a hash-bit width of the first hash algorithm so that data is lost from a first hash in the creation of a corresponding second hash, so that the second hash value cannot be decoded or reversed to obtain the value of the original data element corresponding to the confidential PHI.

18. The method according to claim 14, wherein:
each patient medical record includes a master record number (MRN) assigned by the one data source;
the hashing appliance generates a hash value for the MRN of the patient medical record, and encrypts the hashed MRN using a key provided by the respective source system; and
the source system saves the hashed MRN in a MRN-to-patient table to provide a correspondence between the hashed MRN value and an identity of the patient associated with the patient medical record.

19. The method according to claim 18, wherein:
based on a re-identification request corresponding to a targeted MRN, the master patient index server transmits the encrypted targeted MRN to the source system that originally assigned the MRN to the patient record; and
the source system decrypts the targeted MRN and locates the targeted MRN in the table to re-identify the patient associated with the targeted MRN.

20. A method for anonymizing and aggregating protected health information (PHI) from multiple data sources, the method comprising:
transmitting a plurality of patient medical records to a hashing appliance, each patient medical record containing at least one data element corresponding to confidential protected health information (PHI), the hashing appliance configured to:
append a salt value to each data element corresponding to confidential PHI in each patient medical record;
generate a hash value for each data element corresponding to salted confidential PHI;
replace each data element corresponding to confidential PHI with the corresponding generated hash value to generate an anonymized patient medical record;
cluster the plurality of anonymized patient medical records under a unique patent identifier;
determining if a newly received anonymized patient medical record is related to anonymized patient medical records clustered under unique patient identifier by:
generating a comparison vector by comparing the hash values corresponding to the confidential PHI in the newly received anonymized patient medical record with the hash values of the anonymized patient medical records clustered under the unique patient identifier;
providing a confidence vector that defines a two-dimensional matrix of elements, wherein:
each row in the two-dimensional matrix is associated with one field of possible fields of an anonymized patient medical record,
a first column of the two-dimensional matrix lists elements to be crossed when a value of a field of the newly received anonymized patient medical record matches a value of a corresponding field in a cluster of anonymized patient medical records,
a second column of the two-dimensional matrix lists elements to be crossed when the value of a field of the newly received anonymized patient medical record does not match any values of a corresponding field in a cluster of anonymized patient medical records, and
a third column of the two-dimensional matrix lists elements to be crossed when the value of a field of the newly received anonymized patient medical record is not provided;
selecting elements of the confidence vector based on multiplying the selected elements together to thereby obtain a match confidence level, wherein the match confidence increases with an increase in a magnitude of the match confidence level;
comparing the match confidence level to a predetermined threshold; and
clustering the newly received anonymized patient medical record to the cluster if the confidence level is greater than the predetermined threshold.

* * * * *